Figure 1:
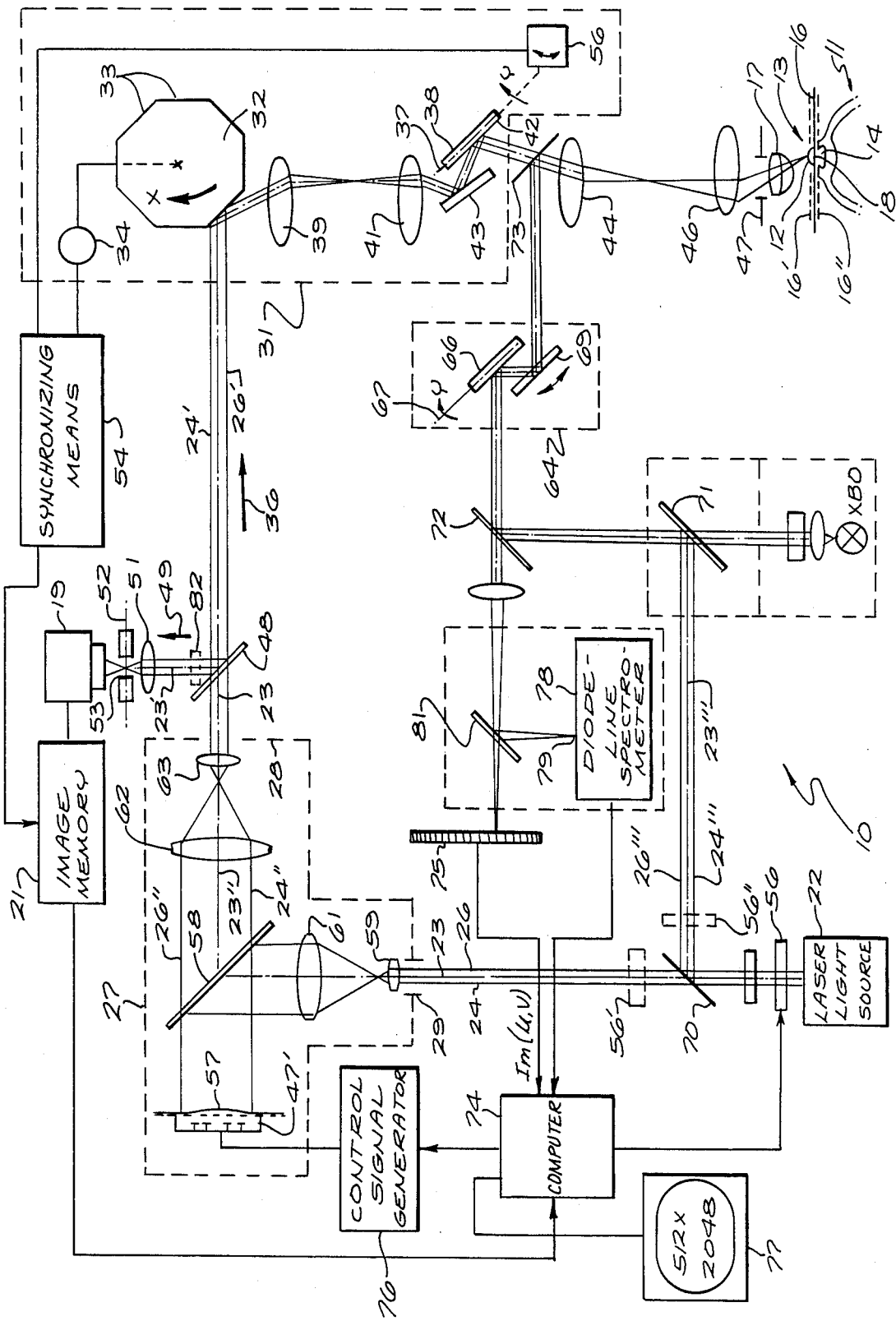

United States Patent [19]

Bille

[11] Patent Number: 4,838,679
[45] Date of Patent: Jun. 13, 1989

[54] APPARATUS FOR, AND METHOD OF, EXAMINING EYES

[76] Inventor: Josef Bille, Am Pferchelhang 2/4, 6900 Heidelberg, Fed. Rep. of Germany

[21] Appl. No.: 706,619

[22] Filed: Feb. 28, 1985

[30] Foreign Application Priority Data

Jun. 14, 1984 [DE] Fed. Rep. of Germany ....... 3422144

[51] Int. Cl.⁴ ............................ A61B 3/10; A61B 3/14
[52] U.S. Cl. ..................................... 351/205; 351/206; 351/221
[58] Field of Search ............... 351/205, 211, 221, 206, 351/207, 208

[56] References Cited

U.S. PATENT DOCUMENTS

| 3,832,066 | 8/1974 | Cornsweet | 351/205 |
| 4,173,720 | 11/1979 | Geluk | 358/111 |
| 4,213,678 | 7/1980 | Pomerantzeff | 351/221 |
| 4,472,029 | 9/1984 | Hardy | 350/500 |

Primary Examiner—Rodney B. Bovernick
Attorney, Agent, or Firm—Ellsworth R. Roston; Charles H. Schwartz

[57] ABSTRACT

This invention enables comprehensive examinations of the front parts of human eyes, reliably provides precise and easily interpretable pictorial representations of the examination field, enables gentle examinations of short duration and is comparatively simple in construction and application. In this arrangement, a confocal arrangement of a pinhole relative to the focal plane of a microscope objective causes a scanning laser light bundle to be focused on the examination field. Use of a microscope objective for focusing the scanning light bundle enables a narrow limitation to be provided in the depth of the examination field. This light bundle may have a relatively wide cross section. Use of a pinhole to focus on a photodetector the light reflected from the eye causes a favorably high signal-to-noise ratio to be produced and image information data to be provided within minimal time intervals such as small fractions of a second to at most a few seconds. An electrically controllable active mirror operable within the beam-shaping optics of the scanning field may be included to displace the plane of the examination field relative to a median position. This active mirror may be controlled to operate as different types of mirrors including a plane mirror. Therefore, data for a high-resolution subdivision of an examination object into a plurality of thin layer-shaped examination fields may be obtained. Such data can be processed by an appropriate computer-controlled display unit and displayed by the unit as representations of the examination object along arbitrarily oriented and/or shaped sectional planes or curved areas.

50 Claims, 2 Drawing Sheets

APPARATUS FOR, AND METHOD OF, EXAMINING EYES

This invention relates to apparatus for examining and representing the human eye. The invention is particularly adapted to examine and detect thin layer-shaped parts of the human eye, especially the front parts of the eye. The invention also relates to methods of examining and representing the human eye.

Apparatus relating to this invention is disclosed by Oleg Pomerantzeff and Robert H. Webb in U.S. Pat. No. 4,213,678. This apparatus constitutes a laser-scanning ophthalmoscope which provides pictorial representations of the eye fundus for diagnostic purposes. A laser light bundle is focused on an eye fundus—the retina—which is scanned point by point with at least one scanning sequence. The intensity of the scanning light is reflected and/or scattered from the eye fundus and is used to generate a pictorial representation thereof in a manner well known from television display techniques.

The scanning laser-light bundle in the Pomerantzeff patent is coupled into an optical path which is used for scanning illumination of the examination object and for detection of the reflected light. The scanning laser-light bundle is coupled into the optical path by a small deflecting mirror which, viewed in the direction of propagation of the reflected light, is arranged immediately before the central part of a convex lens. The convex lens concentrates on a photodetector the light reflected from the examination object to the photodetector. The deflecting mirror is also used to prevent scanning light reflected at the cornea from being directed to the photodetector. As a result, the deflecting mirror acts as a central stop member of a generally ring-shaped entrance pupil of the convex lens. This is possible in the apparatus of U.S. Pat. No. 4,213,678 because there is a considerable axial distance between the cornea (which is not examined) and the eye fundus—the retina—which is examined.

As a result, the bundle cross section propagated within the cornea reflex light in the Pomerantzeff patent is small compared with the bundle cross-section within which light reflected at the cornea is propagating towards the convex lens. This causes the signal-to-noise ratio to be quite high. It will accordingly be seen that the apparatus of U.S. Pat. No. 4,213,673 is suitable at best for examination of the retina of a human eye but not for examination of front parts of the eye.

A precise detection of numerous alterations of the eye itself and also changes in the metabolism resulting in alterations of front parts of the human eye (cornea, front chamber, eye lens and compartments thereof) would enable an early diagnosis and therapy. There is accordingly a considerable demand for apparatus which will provide a detailed information with respect to an internal structure of front parts of the human eye. For example, precise pictorial representations of the front parts of the human eye are of special interest and indispensable with respect to the shaping of lenses, and particularly contact lenses, for compensating visual defects.

Slit-lamp microscopes or equivalent devices commonly used for examinations of the front parts of the human eye require time-consuming manipulations which may be rather cumbersome and aggravating for a person subjected to examination. Furthermore, such slit-lamp microscopes normally are adapted to be used for only a few and special diagnostic purposes and cannot provide for comprehensive diagnoses.

Also known is apparatus including a scanning microscope as proposed by U.s. Pat. No. 4,170,398 to Koester. This apparatus enables examinations of front parts of human eyes. The cornea reflex is suppressed by spatal separation of the reflected or scattered light beam from an illuminting light beam which is transmitted through different parts of the image of an illuminated slit across the examination field. A rotating mirror with three facets rectangularly arranged with respect to one another is used for this purpose. This apparatus suffers from a high sensitivity to misadjustments and it is also difficult and time-consuming to adjust this apparatus to parts of the eye in different planes of examination.

some principle objects of this invention are, therefore, to provide apparatus (a) which enables comprehensive examinations of the front parts of human eyes, (b) which reliably provides precise and easily interpretable pictorial representations of the examination field, (c) which enables gentle examinations of short duration and (d) which is comparatively simple in construction and application.

In the apparatus of this invention, the confocal arrangement of a pinhole with respect to the focal plane of a microscope objective focuses a scanning laser light bundle on the examination field. This confocal arrangement provides for an effective suppression of the cornea reflex. A favorably high signal-to-noise ratio is obtained and, therefore, image information data desirable for a reliable diagnosis may be obtained within minimal time intervals e.g. within small fractions of a second to at most a few seconds. The intensity of the scanning light may be enhanced, when desired, to obtain high-contrast pictorial representations of the examination object.

Use of a microscope objective for focusing the scanning light bundle in the apparatus of this invention enables a narrow limitation in the depth of the examination field. By including an electrically controllable active mirror designed to operate within the beam-shaping optics of the scanning optical path, the plane of the examination field may easily be displaced with respect to a median position. This median position is correlated with the operation of the active mirror. This active mirror may be controlled to operate as different types of mirrors including a plane mirror. Therefore, a high-resolution subdivision of an examination object into a plurality of thin layer-shaped examination fields may be displayed by the apparatus of this invention for a comparative inspection.

Alterations of the refractive power of the active mirror in the apparatus of this invention are obtained by electrostatic forces acting on a metallized membrane which follows without inertia the electrostatic control forces imposed upon the mirror. In this way, displacements of the examination plane within a range of several hundred $\mu$m can be obtained. As a result, no displacements of relatively weighty lens systems are necessary in the apparatus of this invention to displace the focal plane of the imaging microscope objective. This causes a precision in the adjustment of the examination plane to be considerably enhanced.

The apparatus of this invention provides for the storage of image data for a plurality of equidistantly spced examination fields, respectively, which may be planar and may be separated from one another in step-widths of 1 $\mu$m to 10 $\mu$m. Such data can be processed by an appropriate computer-controlled display unit and displayed by the unit as representations of the examination object along arbitrarily oriented and/or shaped sectional planes or curved areas. By providing sufficiently small step-width from examination plane to examination plane and storing the images in such examination planes in an image memory having a sufficiently high storage capacity, the stored image data may be processed in a data processing system to provide a sharp 3D-image of the examination object as seen from arbitrary directions and in any sectional representations.

An additional scanning apparatus may be included in the invention and may be operated at a lower scanning frequency than the main scanning apparatus used to generate the image data characteristics of the examination object. By using such additional scanning apparatus, a point-spread function may be detected for a selected number of image spots within the examination or image field. The point-spread-function describes the spatial intensity distribution for light which is redirected from the image spot into the optical path used for detection.

By proper analysis of the point-spread-function, structures of an image-element smaller than the wavelength of the scanning light may be detected. By comparing the detected, i.e. real, point-spread-function with ideal point-spread-functions as defined by the geometrical-optical boundary conditions, error signals may be generated which may be used to control the active mirror in a manner that spheric and/or astigmatic aberration effects may be compensated. These spheric and/or astigmatic aberrations effects are produced by the test specimens, i.e. by parts of the examination object which are transmitted by the scanning light before it is focused onto the examination plane.

The effect is, so to speak, a "smoothing" of the focal plane of the microscope objective within the scanning optical path. Pictorial representations may accordingly be obtained which, at a highermost degree, are realistic and enable a precise and quantitative evaluation of the front part of the eye. This is of major importance in detecting topographical alterations of front parts of the eye and, in particular, in adapting contact lenses to the eyes of the bearer.

In addition, or alternatively, to an image field scanning, layer-thicknesses of the examined structures may be measured. This is of considerable importance in view of the lachrymal film which may be affected by using contact lenses. It is of particular interest to obtain information of the time within which the lachrymal film may regenerate.

The apparatus of this invention is advantageous in that parts of the eye located in front of the eye lens may be scanned by utilizing UV-radiation of comparatively high intensity without inconveniencing a person subjected to examination. This is of particular interest with respect to high-contrast representations of the endothelial cell layer on the inner surface of the cornea. Since the eye lens is non-transparent for UV-radiation, any undue radiation exposure of the light-sensitive retina is reliably avoided. Favorably high signal-to-noise ratios are achievable for cornea and/or front chamber examinations. In contrast, by utilizing conventional methods, such examinations cannot now be performed.

Figure 2:
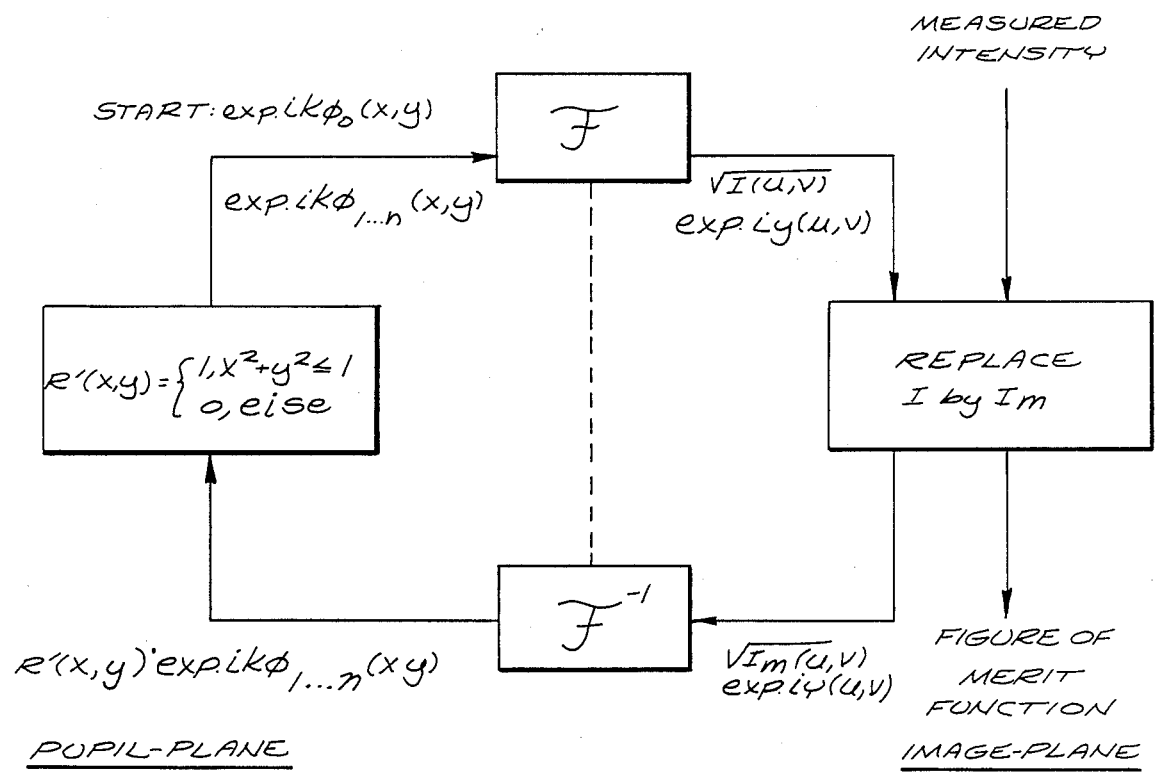
Figure 3:
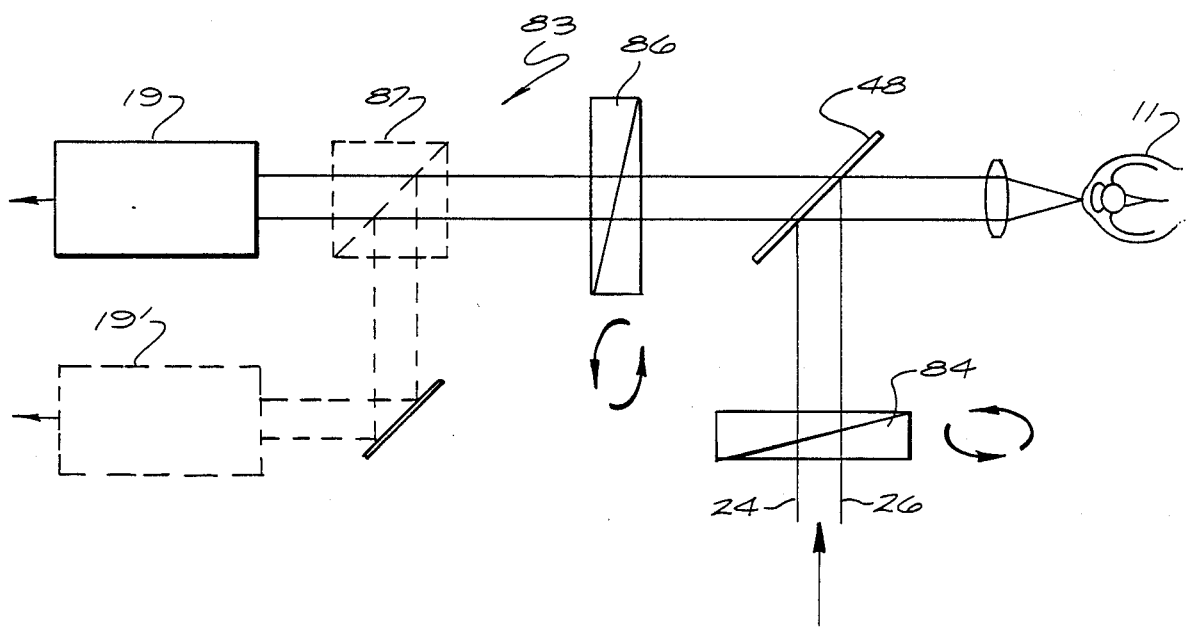

In the drawings:

FIG. 1 is a diagrammatic representation of the apparatus of this invention and shows in detail scanning and processing members for producing an optical path to generate a pictorial representation of a layer-shaped portion of a human eye;

FIG. 2 is a schematic representation of apparatus for provding mathematical analyses to evaluate point-spread-functions and to generate correction signals, in accordance with such analyses, for proper adjustment of an active mirror used to compensate image distortions in the apparatus shown in FIG. 1; and FIG. 3 shows the basic structure of a polarization-sensitive detector for use in the apparatus shown in FIG. 1.

This application corresponds to Application No. P 3422144.1 which has a filing date to June 14, 1984, in the Federal Republic of West Germany and which lists the same inventor as the inventor listed in this application. Applicant accordingly claims the benefit of the Convention data of June 14, 1984, in this application.

Referring to FIG. 1, apparatus 10 according to the invention is shown which is particularly intended to image thin layer-shaped parts of the foreground, i.e., the front parts, of a human eye for diagnostic purposes. Such a human eye is schematically illustrated in FIG. 1 and designated generally by reference numeral 11. By means of the apparatus 10, alterations may be detected of the front parts of the human eye such as the lachrymal film covering the outside of the cornea 12, the cornea 12 itself and/or the eye-lens 14. Furthermore, partial sections or layers of these eye elements may be detected. Such detections may be made at with an optimal accuracy to facilitate a reliable recognition of diseases of the eye itself or of other kinds of diseases. Such diseases may result in alterations of the eye-foreground or parts of the eye.

In the following description of structural and functional properties of the apparatus 10, methods for its appropriate use will be explained. These methods constitute a substantial aspect of the invention.

In its basic structure, the apparatus 10 is a laser-scan-microscope which, in basic analogy to the generation of a television picture, is providing for a line-by-line scanning. Within each scanning line, the apparatus 10 provides for a point-by-point scanning of an examination field 16. The examination field 16 is schematically represented in FIG. 1 by the focal plane of a microscope objective 17. This focal plane is illustratively assumed to be a plane within the endothelial cell layer. The cornea 12 is separated from the front chamber 18 of the human eye by the endothelial cell layer.

In providing this line-by-line and point-by-point scanning, individual field elements (or points) of the examination field 16 are sequentially illuminated with laser-light as by a light source 22. The light source 22 may be a helium-cadmium laser which emits light preferably at wavelengths in the near UV-spectral range and in the violet range of the visible spectrum. Such wavelengths may be illustratively at $\lambda 1 = 325$ nanometers and $\lambda 2 = 440$ nanometers.

The light illuminating the individual field elements is reflected or scattered from the individual field elements in synchronism with the light-scanning of the examination field. The intensity of the laser light reflected or scattered from the examination field is detected by a photoelectric detector such as a photomultiplier 19. The light detected by the photomultiplier 19 may be introduced, in the form of signals, to an image-memory 21 and stored in the image-memory 21 for further processing. For example, the information stored in the image-memory 21 may be used for image generation and/or computational processing.

The laser constituting the light source 22 may be a continuous wave laser which is continuously light-emitting. In FIG. 1, the primary light bundle of this He-Cd-laser is represented by a dash-dotted central beam 23 and by marginal beams 24 and 26. The primary light bundle 23, 24 and 26 of the He-Cd laser 22 is a substantially parallel bundle having a cross-section of about one (1) square millimeter (1 mm$^2$).

The laser-light bundle may be shaped by means of beam-shaping optics generally indicated in broken lines at 27. By such shaping, the output light bundle emerging from the beam-shaping optics 27 and defined by marginal beams 24' and 26' has a larger cross section than the light bundle has at an input 29 of the beam shaping optics 27. As a result, an appropriate adjustment is made in the bundle cross section to facilitate optical arrangements and to provide for optical processing, and appropriate adjustment, in the convergence of the laser-light bundle to an object to be described hereinafter in some more detail. The output light bundle emerging from the beam shaping optics 27 is indicated at 23', 24' and 26'.

The output light bundle 23', 24' and 26' is directed to a first scanning sub-assembly shown in broken lines and indicated generally at 31. The scanning sub-assembly 31 provides for horizontal and vertical deflections of the beam. These beam deflections enable scanning of an examination field 16 in the X- coordinate direction and a Y-coordinate direction. As a horizontally deflecting element in the scanning sub-assembly 31, a polygonal mirror 32 is provided with facets such as shown in FIG. 1. These facets may define an octagon having eight (8) equal sides. In a typical form, however, the polygonal mirror may have as many as 24 facets in an equilateral polygonal relationship.

The polygonal mirror 32 is driven rotationally. The rotational frequency of the polygon mirror 32 is synchronized with the input into the photomultiplier 19 of the data relating to the light intensity. This synchronization occurs in the image memory 21, in which the image of the examination field 16 is stored in digital format.

Seen in the direction of an arrow 36 corresponding to the direction of propagation of the laser-light bundle 23, 24' and 26', the Y-deflection member is arranged subsequent to the X-deflection members 32 and 34. The Y-deflection element is provided by a pivotably driven galvanometer-mirror 38 which is pivotable relative to a horizontal axis 37.

By means of a telecentric optical path which comprises two lenses 39 and 41 in a 4-f-arrangement (f=the focal length of each of the lenses 39 and 41), the light directed to the facets 33 of the polygonal mirror 32 is imaged on the reflecting surface of the galvanometer-mirror 38. A deflecting mirror 43 is disposed between the galvanometer mirror 38 and the exit lens 41 of the telecentric optical path defined by the lenses 39 and 41. The deflecting mirror 43 is provided to obtain an appropriate geometry of the optical path.

A telecentric arrangement defined by lenses 44 and 46 is analogous to the telecentric arrangement defined by the lenses 39 and 41. The telecentric arrangement defined by the lenses 44 and 46 provides for the imaging of the reflecting surface 42 of the galvanometer mirror 38 on an entrance pupil 47 of the microscope objective 17. The microscope objective 17 focuses onto the examination plane 16 the laser light passing through the entrance pupil 47 as a parallel or nearly parallel bundle.

Any laser light reflected and/or scattered by any inhomogeneities in the focusing or examination field plane 16 is redirected into the scanning optical path described previously and is diverted from this scanning optical path, in a direction indicated by an arrow 49, by a partially transparent mirror such as a semi-transparent mirror. The light rflected in the direction 49 is in the form of a light bundle 23', 24' and 26'. This light bundle is focused by a further microscope objective 51. A pinhole 53 is disposed in the focal plane 52 of the microscope objective 51. The pinhole 53 limits the bundle so that the only light passing through the pinhole 53 is that which emerges from a portion of the examination field corresponding to the depth of focus of the microscope objective 17. The light passing through the pinhole 53 is used for intensity measurements.

The photomultiplier 19 is disposed behind the pinhole in the direction 49 in which the light in the bundle 23', 24' and 26' is propagated. The photomultiplier 19 generates an output signal in proportion to the intensity of the laser-light which is redirected (reflected and/or scattered) from the examination field 16 into the scanning optical path.

The generation of the output signals by the photomultiplier 19 is controlled by a synchronizing means 54 which controls the rotation of the polygonal mirror 32 and the pivotal movements of the galvanometer mirror 38, the latter with the help of a pivot drive 56. The output signals generated by the photomultiplier 19 for each of the point-shaped elementary parts of the examination field 16 are stored in the image memory 21.

The examination field 16 may be displayed by a television monitor to generate an image representation of the examination field 16. For example, the examination field may be subdivided such as into 512×2048 elementary image points. In accordance therewith, 512 lines are scanned, and within each line 2048 image points are scanned. This is analogous to the generation of a normal television picture. The size, i.e. the dimensions, of the elementary image points in the "horizontal" and "vertical" directions then results from a horizontal extension of the examination field 16 divided by the numnber of elementary image points in each line, and from a "height" of the examination field divided by the number of lines in the field. The size of the examination field 16 may be variable between 100 $\mu$m (micrometers) and several mm (millimeters) in accordance with the focal length of the microscope 17. Consistent therewith, the size of the elementary image points may be variable between 0.05 $\mu$m and several $\mu$m.

Scanning of the examination field 16 occurs so fast that the image area is scanned within 40 ms (milliseconds), every 20 ms (milliseconds) half-image being generated. One of these half images is formed from the even lines and the other half image is from the odd lines. These half images are interlined in a manner which is well known in the art.

The storage of the output signal from the photo-multiplier 19 in synchronism with the scanning movements of the polygonal mirror 32 and the galvanometer mirror 38 is achieved in a manner well known in the art. This is described in a scientific publication in 1979 by Shack et al (R. Shack, R. Baker, R. Buchroeder, D. Hillmann, R. Shoemaker and P. H. Bartels), in the Journal of Histochemistry and Cytochemistry at Vol. 27, page 153.

An electro-optical or an acousto-optical modulator is also synchronized with the read-in frequency of the image memory 21. The modulator controls the intensity with which the scanning light beam is directed to the examination field 16. Thereby, selected portions of the examination field 16 may be illuminated with a greater light intensity than other portions of the field. This is particularly important in applications where selected portions of the examination field are imaged with high contrast, but where the average light exposure of the examination object is to be maintained as low as possible.

To provide for the capability of scanning in a short time sequence in a plurality of spaced examination fields or planes 16, 16' and 16'', an active mirror 57 is provided. By an electrical control, a positive or negative refractive power can be imparted to the mirror 57 to enable an alteration in the position of the examination plane 16. This alteration may be within a range of +200 μm relative to a preselected position of the examination plane 16 as seen in a direction perpendicular to the plane 16. If no control signal is applied to the active mirror 16, the mirror acts as a planar mirror.

The active mirror 57 is disposed in a pupil plane 47' which corresponds optically to the plane of the entrance pupil 47 of the microscope objective 17. The mirror 57 is illuminated by a partially-transparent—normally, a semi-transparent -mirrow 58 which is included in the beam-shaping optics 27. The mirror 58 receives the laser output light bundle 23, 24 and 26, after the light bundle has been widened in its cross section through the action of the arrangement defined by the telecentric lenses 59 and 61. The lenses 59 and 61 may be convex lenses of different focal lengths.

After reflection at the active mirror 57 and transmission through the partially transparent mirror 58, the light bundle represented in FIG. 1 by the margin-defining beams 26 and 24 passes a second telecentric arrangement of lenses 62 and 63 included in the beam shaping optics 27. As a result, the cross section of the light bundle 23, 24 and 26 emerging through the aperture 28 at the exit of the beam-shaping optics 27 is adjusted to a size appropriate for the processing of the laser light bundle within the first scanning apparatus 31.

By appropriate control of the active mirror 57, the apparatus 10 may be rapidly and precisely adapted to scan different examination fields such s the equidistantly spaced examination fields 16, 16' and 16''. With a sufficient storage capacity in the image-memory 21, the total yield of the image data obtained from a scanning of all of the different examination fields may be stored in the image memory 21. The contants of the image memory 21 may then be processed to generate pictorial representations of the examination object along arbitrary section planes which may be perpendicular, parallel or inclined with respect to the scanned examination fields such as the examination fields 16, 16' and 16''. Thus, with respect to inspections of front parts of a human eye, pictorial representations may be obtained which provide the same information as is obtainable by using conventional slit-lamp microscopes.

When scanning the different examination fields such as the examination fields 16, 16', and 16'' as described in the previous paragraphs, the pictorial representations obtained are burdened with minor blurs. These blurs may arise from the circumstance that light before and behind the examination fields 16, 16' and 16'' in the direction of movement of the light may contribute to the intensity distribution of the laser light which is detected by the photomultiplier 19. Successive scanning of the progressive examination fields 16, 16' and 16'', however, offers the opportunity to reliably recognize aberrations in such pictorial representations so that light from other planes than the focal plane, such as the plane 16, are rejected and only the light from the focal plane 16 remains.

By processing in the image memory 21 and the computer 74 the contents representing the different examination fields such as the fields 16, 16' and 16'', sharp and high-contrast pictorial representations of the inspected structures may be obtained. This may be achieved by proper use of the 3-dimensional transfer function of the microscope objective 17. This 3-dimensional transfer function is well known in the art. Since the computational correction of the picture quality can be provided with respect to any of the examination planes 16, 16' and 16'', pictorial representations can be generated with a quality as if the depth of focus of the microscope objective 17 were infinite.

As described above, a characteristic feature of the apparatus 10 is the confocal arrangement of the pinhole 53 relative to the focal plane of the microscope objective 17. This focal plane corresponds to the examination field 16. This arrangement is instrumental in insuring that the light passing through pinhole 53 has the the same depth of focus as an image generated by the microscope objective 17. Because of the confocal arrangement of the pinhole 53 relative to the image generated by the microscope objective 17, light reflected from parts of the examination object disposed in front of, or to the rear of, the examination field (when viewed in the direction of propagation of the laser light) is directed to the walls defining the pinhole 53. Such light is thereby prevented from contributing to the intensity of the output signal produced by the photo- multiplier 19. This is of particular importance with respect to inspections of individual parts of a human eye such as the endothelial layer arranged between the cornea 12 and the front chamber 18.

The refractive index of the endothelial layer is only slightly different from that of the chamber liquid retained in the adjacent front chamber 18 of the eye 11. As a result, the reflectivity of the endothelial layer is small compared with the reflectivity of the cornea 12. For example, the reflectivity of the endothelial layer is only one hundredth (1/100) of the reflectivity of the corena 12. Nevertheless, in the apparatus 10, the contribution to the output signal from the photomultiplier 19 of the light reflected at the lachrymal film 13 is negligible. One reason is that, in adjusting the apparatus 10 for scanning the endothelial layer, the lachrymal film 13 is removed from the depth of focus of the microscope objective 17. Furthermore, as the cross sectional area of the laser light bundle 23', 24' and 26' is increased and the focal length of the microscope objective 17 with respect to light reflected from the lachrymal film 13 is decreased, the contribution to the output signal from the photomultiplier 19 is decreased.

In a typical dimensional layout of the apparatus 10, the microscope objective 17 has a focal length of approximatley five millimeters (5 mm) and a numerical aperture of 0.9 and the diameter of the laser-light bundle 23', 24' and 26' focused by the microscope objective 17 on the examination field 16 has a value to approximately six millimeters (6 mm).

With a proper choice of the microscope objective 17 and of the cross-sectional area of the light bundle, a resolution of less than 0.5 μm may be achieved. For inspections of the lachrymal film 13, the cornea 12 and/or the endothelial layer which is disposed between the cornea 12 and the front chamber 18, light of relatively short wavelengths such as the wavelengths emitted by the He-Cd laser 22 is provided. Such relatively short wavelengths are advantageous because the eye lens 14 is non-transparent to such wavelengths. As previously described, such wavelengths may be in the order of λ1=325 nm.

In examinations where light of the wavelength λ1=325 nm may be used, the scanning light may be provided with high intensities without affecting the retina. On the other hand, for an inspection of structural aberrations in the eye lens 14, light emitted by the laser 22 with an increased wavelength such as a wavelength of λ2=440 nm is provided for scanning the examination field.

As a result of inhomogeneities or irregularities in a layer or part of the examination object through which the scanning light is transmitted before it is focused onto the examination field 16, the focal plane (which, by tacit implication, has been assumed to be a flat and smooth plane) may be deformed as a result of aberrative and/or astigmatic effects. Such image distortions may result in at least partially blurred images. To compensate for such deformations in the focal plane, a scan—apparatus shown in borken lines and generally indicated at 64 is provided. The scan-apparatus 64 functions in the same manner as described above for the scan apparatus 31 and enables a partial or complete scanning of the examination field 16.

The apparatus 64 includes as its scanning elements first and second galvanometer mirrors 66 and 68. The first galvanometer mirror 66 is pivotable about a horizontal axis 67 parallel to the plane of propagation of the scanning light. the galvanometer mirror 66 provides for a Y-deflection of the scanning light. The galvanometer mirror 68 is pivotable about an axis which extends perpendicular to the plane of propagation of the scanning light. The galvanometer mirror 68 provides for an X-deflection i.e. the line-deflection of the scanning light.

The light provided within the scanning apparatus 64 for scanning the examination object is a partial light bundle 23'', 24'' and 26''. This light bundle is branched from the primary light bundle 23, 24 and 26 of the laser 22 by a beam splitter 70, such as a partially transparent mirror. As shown in FIG. 1, the partial light beam 23'', 24'' and 26'' is deflected by a first partially transparent mirror 71 to a second partially transparent mirror 72 and is directed from the mirror 72 into the scanning apparatus 64. The llight beam 23'', 24'' and 26'' then passes to a third partially transparent mirror 73.

The partially transparent mirror 72 is disposed between the galvanometer mirror 38 in the scanning apparatus 31 and the telecentric arrangement defined by the lenses arrangement 44 and 46. The intensity of the partial light beam 23'', 24'' and 26'' is only about ten percent (10%) of the intensity of the primary light beam 23, 24 and 26 from the laser 22. The light beam from the partially transparent mirror 73 is coupled into the optical path for imaging the examination field 16.

The operational mode of the scanning apparatus 64 is asynchronous with respect to the scananing apparatus 31 and the scanning frequency of the scanning apparatus 64 is considerably lower than that of the scanning apparatus 31. Light reflected and/or scattered at the examination object and thereby redirected into the optical path of the scananing apparatus 64 is detected by a 2D-matrix-array of photoelectric detectors, preferably a diode matrix 75.

In this way, in response to each illumination of an image spot or element of the examination field, a two-dimensional intensity distribution of radiation is redirected (reflected and/or scattered) from the examination field 16 into the optical path of the scanning apparatus 64. This two-dimensional intensity distribution or radiation is detected by the diode matrix 75 to provide a point-spread function. This function is stored in a data processor for further processing.

By using well known mathemtical algorithms the basic structures of which will be explained, calculations may be made, from the point-spread function, of deviations in the shape of the wavefront of light which has passed through parts of the examination object. These deviations represent variations from an ideal shape of the wavefront which would be normally expected if no examination object were present. Deviations of the point spread function from an ideal shape may be interpreted to indicate that the examination object is affected by untypical aberrations.

The detection of the point-spread function is also of particular interest because it represents aberrations which are even smaller, in the distribution of the spot-image structures, than those of the scanning spot or the scanned elements of the examination field. The information obtained from an evaluation of the point-spread function with respect to the shape of the wavefront of the scanning light may be interpreted to represent a "deformation" in a focal plane of the microscope objective 17. This information may also be used to activate the active mirror 57 to compensate for such deformations.

As a result, the data provided by the scanning apparatus 64 and representing the point-spread function may be used to monitor a variable for signals which correct the activation of the active mirror 57. These correcting signals may be applied to the active mirror 57 to compensate for the image distortions from which the deformations of the wavefront and the focal plane occur. This compensation is achieved in the direction in which the examination field 16 is being scanned by the scanning apparatus 64.

The evaluation of the data representing the point-spread function is provided by a computer 74. In response to output signals from the computer 74, a control-signal generator 76 produces control signals to obtain an appropriate compensatory adjustment of the active mirror 57. The computer 74 is also used as a display control unit which, by an appropriate processing of the intensity data stored in the image memory 21, enables the display of images of the examination object in a desired variety of section planes.

Reference is now made to FIG. 2, which is a schematic representation of a computational procedure for processiing in the computer 74 the data relating to the point-spread function. This procedure basically consists in producing an iteration in which the intensity distribution (of the point-spread function) Im (u, v) (u=line index, v=column index of the diode matrix) is used to calculate, for the plane of the entrance pupil 47 of the microscope objective 17, a shape of the wavefront of the scanning light. This shape is consistent with the detected intensity distribution Im (u, v). As a reasonable initial condition, no deformation occurs in the focal plane and the radiation field at the location (x, y) of the entrance pupil 47 of the microscope objective 17 has a plane wavefront which is characterized by a phase factor $\phi(x, y)$.

The transfer function of the optical system includes a typical structure of that part of the examination object to which the scanning light beam passes, i.e. the light distribution in the image plane is derived by a convolution of the wavefront $R(x,y) \cdot \exp ik\ \phi(x,y)$ with the transfer function. In consideration of such transfer function, the shape of the radiation (light)-field $\sqrt{I(u, v)} \exp i\gamma(u,v)$ in the focal plane of the microscope objective 17 is calculated. The amplitude factors $\sqrt{I(u, v)}$ may be replaced by the values $\sqrt{Im(u, v)}$. Such values may be obtained from the intensity measurements and from the application of the inverse transfer function $F^{-1}$ to the shape of the radiation light-field in the focal plane of the microscope objective 17. By replacing the amplitude factors $\sqrt{I(u, v)}$ by the values $\sqrt{Im(u, v)}$, a shape of the wavefront at the entrance pupil 47 of the microscope objective 17 is calculated which is consistent with the set-up field-shape. This shape has a phase factor $\phi_1(x, y)$ consistent with the set-up field-shape.

In a first iteration step, the phase factor $\phi_1(x, y)$ is set up for a mathematical description of the radiation field at the location of the entrance pupil 47. The radiation field in the focal plane of the microscope objective 17 is again calculated. As a result, the amplitude-factors are replaced by the square-roots of the measured intensities and a new phase factor $\phi_2(x, y)$ is calculated. Such iteration steps are repeated until the measured intensities agree within tolerable limits with the calculated intensity values. In this way, a wavefront at the position of the entrance pupil 47 of the microscope objective 17 is determined. This wavefront is consistent with the measured intensity values.

By comparing the wavefront shapes resulting from the interation procedure, the wavefront at the entrance pupil of the microscope objective 17 for an ideal case with control signals can be generated, through the operation of the computer 74 and the control signal generator 76, for adjusting the active mirror 57. The active mirror 57 is adjusted to make the measured intensity distribution Im (x, y) substantially identical with an ideal intensity distribution in the focal plane of the microscope objective 17. This ideal distribution would result if the radiation field wavefront at the entrance pupil 47 of the microscope objective 17 were ideal. In this way, the transfer function of the optical system can be adjusted to smoothen the focal plane 16 of the microscope objective 17 and to insure that the image information from the first scanning apparatus 31 corresponds to that which would be obtained under ideal imaging conditions. In other words, the transfer function of the optical system is adjusted to achieve a realistic image of the examination field 16.

In the apparatus 10, further provision is made to couple light with a broad-band spectral distribution into the optical path of the scanning apparatus 64. This provides for the capability of measuring optical thicknesses of layer structures, e.g. of the lachrymal film and/or the corenea, respectively, for selected parts of the examination field 16, in particular those parts of the examination field which are inspected by the "fast" scanning apparatus 31. The layer thickness of these structures are detected point by point. Values of detection as high as one thousand (1000) per second can be measured. The measurement of layer thickness is accomplished by using the principles of white-light interferometry to determine the wavelengths of constructve interference. To measure layer thickness, a diode-line-spectrometer 78 is provided with an entrance slit 79. The slit 79 receives light passing from the test object and reflected by a partially transparent mirror 81. A xenon-high pressure lamp is preferably used as a white light source. Because of the use of the He-Cd-laser 22 as a scanning light source, the apparatus 10 may also be used to record the spatial distribution of liminescent molecules within the inspected parts of an examination object. To accomplish this, a filter 82 may be disposed between the photomultiplier 19 and the partially transparent mirror 48. The filter 82 is transparent for the luminescence radiation from the test object but non-transparent for the luminescence exciting radiation of the laser in the ultra-violet range and the radiation in the visible spectral range. Measurements of luminescence radiation are of interest in view of a determination of the distribution of fluorescent proteins in the front chamber liquid.

A polarization-sensitive detection arrangement 83 as shown in FIG. 3 may be used in the apparatus 10 to recognize and image polarizing structures of the examination object provided that polarized light is used to scan the test field. A quarter wave plate 84 is installed in the scanning light path 24 nd 26 and is provided to vary the polarization state of the polarized laser light. As an analyzer, the quarter wave plate 86 may be disposed in the optical wave path and may be provided with an adjustable azimuthal orientation. The quarter waveplate 86 is disposed between the partially transparent mirror 48 and the photodetector 19 and/or a photodetector 19'. The intensity characteristics of the output signals from the detector 19' are stored in the image memory 21 to indicate intensity characteristics.

As shown in FIG. 3 by full lines, when only the photo detector 19 and the two quarter wave plates 84 and 86 are provided, the quarter wave plates 84 and 86 are adjusted to the same state of polarization. The intensity of the output signal from the photomultiplier 19 then is a measure of the number of polarizing structures which are present in the examination object in the orientations defined by that of the polarizer and the analyzer. By equal adjustments of the polarizer and analyzer in direction and amount, the different orientations of such polarizing structures within the examination field 16 may be detected and imaged.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for detecting aberrations in the characteristics of a patient'e eye,
   means for providng a relatively broad beam of light,
   means for directing the beam of light toward the patient's eye,
   means including an entrance pupil displaced a particular distance from the patient's eye for focusing at the entrance pupil the light beam traveling to the patient's eye,
   means for directing from the patient's eye the light beam reflected from the patient's eye,
   a photodetector, a pinhole displaced by the particular distance in front of the photodetector in the direction of travel of the light beam reflected from the patient's eye, and means disposed in front of the photodetector and the pinhole, in the direction of travel of the light beam from the patient's eye, for focusing the light beam at the pinhole to produce at the photodetector signals representing the characteristics of the patient's eye.

2. In a combination as set forth inc iaim 1, means for processing the signals at thephotodetctor to indicate the characteristics of the patient's eye.

3. In a combination as set forth in claim 2, means for scanning the light beam across the patient's eye in a first direction, and means for advancing the beam in a second direction after each light scan in the first direction.

4. In a combination as set forth in claim 1, the means providing the beam of light providing light in the range of approximately 325–440 nanometers.

5. In a combination as set forth in claim 4, means including an active mirror adjustable to compensate for aberrations in the characteristics of the patient's eye.

6. In combination for detecting aberrations in the characteristics of an examination field in the front part of a patient's eye, means for providing a laser light beam with wave lengths in the range of approximately 325–440 nanometers, means for directing the beam of laser light toward the patient's eye while eliminating only peripheral portions of the beam, means including an entrance pupil disposed at a particular distance from the examination field in the front part of the patient's eye for focusing at the entrance pupil the laser light beam traveling toward the patient's eye, a photodetector, means for directing toward the photodetector the light reflected from the patient's eye while eliminating only peripheral portions of such light, a pinhole displaced by the particular distance from the photodetector and disposed in front of the photodetector to limit the width of the beam of light passing to the photodetector, and means for focusing at the pinhole the light passing through the pihole to the photodetector.

7. In a combination as set forth in claim 6, means for scanning the light in first and second coordinate directions, as the light is traveling from the beam-providing means toward the patient's eye, to obtain a raster scan of the light beam.

8. In a combination as set forth in claim 6, means for compensating for blurring of the image represented by the light reflected from the patient's eye.

9. In a combination as set forth in claim 7, means responsive to aberrations in the characteristics of the patient's eye for adjusting the light beam traveling to the patient's eye for compensating for such aberrations.

10. In a combination as set forth in claim 9, means for synchronizing the raster scan of the light beam traveling toward the patient's eye.

11. In a combination as set forth in claim 6, means for adjusting the distance between the focal position near the patient's eye and an examination plane in the patient's eye to obtain an examination of different planes defining the patient's eye.

12. In a combination as set forth in claim 7, means for providing a point-spread function to determine distortions in the image in the examination field at the front part of the patient's eye, and means for using such point-spread function to compensate for such distortions in the image in the examination field at the front part of the patient's eye.

13. In combination for detecting aberrations in the characteristics of a patient's eye, means for providing a beam of light having a relatively low intensity, means for directing the beam of light of relatively low intensity to the patient's eye means including an entrance pupil disposed at a particular distance from the examination field in the patient's eye for focusing the beam at the entrance pupil, means for providing an adjustment in the examination field being viewed at the patient's eye, a photodetector, means for directing in a beam toward the photodetector the light reflected from the examination field in the patient's eye, a pinhole disposed at the particular distance from the photodetector in the direction of travel of the beam directed toward the photodetector, and means for focusing the reflected beam of light at the pinhole.

14. In a combination as set forth in claim 13, means for using a point-spread function to detect if there are distortions in the examination field of the patient's eye.

15. In a combination field as set forth in claim 13, adjustable optical means disposed in a plane optically corresponding to the examination field of the patient's eye, means for directing toward the optical means at least a portion of the beam of light traveling toward the patients eye to obtain a reflection of such light toward the patient's eye, and means for adjusting the adjustable optical means to provide for a scanning of different examination fields in the patient's eye.

16. In a combination as set forth in claim 13, means for detecting, in the light reflected by the patient's eye, blurs resulting from light in other examination fields than the examination field to be detected, and means including adjustable optical means for compensating for the blurs resulting from light in the other examination fields than the examination field to be detected.

17. In a method of detecting aberrations in the characteristics of a human eye in an examination plane at the front of the eye, the steps of:

directing a light beam toward the human eye, focusing the light beam at a first particular position displaced by a particular distance from the examination plane in front of the human eye in the direction of travel of the light beam, directing the light through an entrance pupil at the focal position, directing toward a photodetector the light reflected from the eye, focusing the reflected light beam at a second position displaced by the particular distance from the photodetector in front of the photodetector in the direction of travel of the reflected light beam, passing the reflected light beam through a pinhole at the second position of focus, and processing the photodetector signals to indicate the characteristics of the patient's eye in the examination plane.

18. In a method as set forth in claim 17, the step of compensating in the processed signals for the aberrations in the patient's eye at the examination plane.

19. In a method as set forth in claim 18, the step of:

providing a raster scan of the light beam traveling toward the patient's eye to obtain indications of the characteristics of the patient's eye at different positions the eye in the examination plane.

20. In a method as set forth in claim 17, the steps of:

providing an adjustable path in the travel of the light beam toward the patient's eye, and producing adjustments in the path of travel of the light beam toward the patient's eye to compensate for aberrations in the patient's eye in the examination plane.

21. In a method of detecting aberrations in the characteristics of an examination plane at the front portion of a patient's eye, the steps of:

directing a light beam of relatively low magnitude toward the patient's eye the light beam having a wavelength in the order of approximately 325–440 nanometers, focussing the light beam at a first particular position near, and in front of, the patient's eye to pass the light in the operative width of the beam, directing the focussed light through an entrance pupil at the focussed position, the entrance pupil being displaced by a particular distance from the examination plane, directing toward a photodetector light reflected from the patient's eye, focussing the reflected light beam at a second particular position near, and in front of, the photodetector, passing the focused light beam through a pinhole at the second particular position, the pinhole being displaced by the particular position from the photodetector and processing the signals produced at the photodetector by the light beam to determine the characteristics of the patient's eye in the examination plane.

22. In a method as set forth in claim 21, the steps of:

scanning the first light beam in the examination plane at a first frequency, directing a portion of the scanned beam of light through the focussing means and the entrance pupil to the examination plane of reflection by the patient's eye, scanning the portion of the beam of light at a second frequency different from the first frequency, detecting the light reflected by the patient's eye and scanned at the second frequency to produce signals having characteristics in accordance with the characteristics of such reflected light, processing the last mentioned signals to produce signals representing aberrations in the characteristics of the patient's eye in the examination plane, and correcting the processed signals produced from the photodetector in accordance with the characteristics of the signals representing the aberrations in the characteristics of the patient's eye in the examination plane.

23. In combination for measuring the characteristics of a patient's eye at different positions in an examination field, means for providing a light beam, means for directing the light beam toward the examaination field of the patient's eye, means for focussing the light beam at a particular distance from the examination field of the patient's eye, the light being reflected from the patient's eye at the examination field, photodetector means for producing signals in accordance with the light reflected from the examination field, means for focussing the reflected light at the particular distance from the photodetector means, means for separately processing a portion of the light beam and for directing such separately processed portion to the examination field at the patient's eye for reflection by the patient's eye, means for receiving the separately processed portion of the light beam reflected from the patient's eye, and means responsive to the characteristics of the separately processed portion of the light beam received by the last mentioned means for compensating for three-dimensional aberrations in the image reflected by the patient's eye at the examination field.

24. In a combination as set forth in claim 23, the compensating means including means for storing the signals from the photodetector means for different positions in the examination field of the patient's eye, computer means for processing such stored signals, means for determining three-dimensional variations at individual positions in the examination field and means responsive to the processed signals from the computer means for the individual positions in the examination field and to the signals representing the three-dimensional variations at such individual positions for adjusting the characteristics of the light beam directed toward the examination field of the patient's eye at such individual positions to compensate for the three-dimensional variations in the image reflected by the patient's eye in the examination field at such individual positions.

25. In a combination as set forth in claim 24, the adjusting means including an active mirror and a control signal generator for adjusting the active mirror at individual positions on the active mirror in accordance with the processed signals from the computer means and the signals representing the three-dimensional variations at such individual positions.

26. In a combination as set forth in claim 24, means for determining the point-spread function of the patient's eye at the individual positions in the examination field, means for providing an ideal point-spread function for the individual positions in the examination field, means for comparing the determined and ideal point-spread functions at the individual positions in the examination field to generate error signals representative of any difference between them, and means for introducing the error signals to the computer means for use by the computer means in generating the processed signals.

27. In a combination as set forth in claim 24,
the light beam having wavelengths in the order of approximately 325–440 nanometers, the examination field being at the front of the patient's eye,
the means for focussing the light at the examination plane in the patient's eye including an entrance pupil located a particular distance from the examination field,
the focussing means at the detector including a pinhole located the particular distance from the photodetector means.

28. In combination for measuring the characteristics of a patient's eye at different positions in an examination field,
means for providing a light beam,
means for directing the light beam toward the examination field of the patient's eye,
means for focussing the light beam at a particular distance from the examination field of the patient's eye,
the light being reflected from the patient's eye at the examination field,
photodetector means for producing signals in accordance with the light reflected from the examination field,
means for focussing the reflected light at the particular distance from the photodetector means, and
means responsive to the signals from the photodetector means for varying the examination field being viewed in the patient's eye.

29. In a combination as set forth in claim 28,
the varying means including means for storing the signals from the photodetector means for different positions in the examination field of the patient's eye and computer means for processing such stored signals and means responsive to the processed signals from the computer means for adjusting the characteristics of the light beam directed toward the examination field to vary the examination field of the patient's eye.

30. In a combination as set forth in claim 28,
the varying means including a computer for processing the signals from the photodetector means, an active mirror and a control signal generator for adjusting the active mirror at individual positions on the active mirror in accordance with the processed signals from the computer.

31. In a combination as set froth in claim 29,
means for determining the point-spread function of the patient's eye at the examination field,
means for providing an ideal point-spread function for the examination field,
means for comparing the determined and ideal point-spread functions at the examination field to generate error signals representative of any difference between them, and
means for introducing the error signals to the computer for use by the computer in generating the processed signals.

32. In a combination as set forth in claim 28,
the means for focussing the light a particular distance from the patient's eye including an entrance pupil disposed at the particular distance from the patient's eye, and
the means for focussing the light a particular distance from the photodetector means including a pinhole and a photodetector displaced by the particular distance from the pinhole.

33. In a combination as set forth in claim 32,
the examination field being at the front of the patient's eye and
the means for providing the light beam including means for providing light at a wavelength in the range of approximately 325–440 nanometers.

34. In combination for measuring the characterstcs of a patient's eye at different positions in an examination field,
means for providing a light beam,
means for scanning the light beam at a first particular frequency,
first means for focussing the light beam at a particular distance from the examination field of the patient's eye,
the focussed light beam being reflected from the patient's eye,
photodetector means for receiving the reflected light and for producing signals in accordance with the light received,
second means for focussing the reflectd light at the particular distance from the photodetector means,
means for providing a scanning of the light beam at a second frequency different from the first frequency and for directing the scanned light beam through the first focussing means to the examination field of the patient's eye to obtain a reflection of the scanned light beam by the patient's eye,
means responsive to the reflected light beam scanned at the second frequency for producing signals in accordance with such reflected light beam to indicate a point-spread function, and
means responsive to the signals representing the point-spread function for adjusting the characteristics of the light beam being scanned at the first frequency.

35. In a combination as set forth in claim 34,
means responsive to the signals representing the point-spread function at individual positions in the examination field of the patient's eye for modifying the signals produced by the photodetector means to correct for aberrations in the patient's eye at such individual positions in such examination field.

36. In a combination as set forth in claim 34,
the first focussing means including an entrance pupil displaced by the particular distance from the examination field, and
the second focussing means including a pinhole displaced by the particular distance from the photodetector means.

37. In a combination as set forth in claim 35,
the adjusting means including an active mirror responsive to the light beam being scanned at the first frequency for introducing the light beam to the scanning means, the active mirror being constructed to provide for modifications in the characteristics of the light beam at individual positions in the light beam, the modifying means further including means for introducing to the active mirror the signals representing the point-spread function at individual positions in the examination field to modify the characteristics of the active mirror at the individual positions in accordance with the characteristics of the signals representing the point-spread function at such individual positions.

38. In a combination as set forth in claim 36,
the examination field being at the front of the patient's eye and the light beam having a wavelength in the range of approximately 325–440 nanometers.

39. In combination for measuring the characteristics of a patient's eye in an examination field at the front part of the patient's eye,
means for providing a light beam,
means for scanning the light beam at a first frequency,
first means for focussing the light beam at a particular distance from the examination field,
the light beam being reflected from the patient's eye,
photodetector means,
second means for focussing the reflected light beam at the particular distance from the photodetector means,
means for scanning the light beam at a second frequency different from the first frequency and for directing the light beam through the first focussing means to the examination field,
means responsive to the light scanned at the second frequency and reflected from the patient's eye to generate correctional signal, and
means responsive to the correctional signals for adjusting the characteristics of the light beam at the individual positions in the examination field in accordance with the characteristics of the correctional signals.

40. In a combination as set forth in claim 39,
an active mirror disposed in the path of the light beam passing to the examination field and being scanned at the first frequency, the active mirror being constructed to provide a field adjustable at individual positions and responsive to signals introduced to the active mirror to provide adjustments in the field of the active mirror,
means responsive to the correctional signals for processing the correctional signals, and
means for introducing the processed correctional signals to the active mirror to obtain adjustments in the field of the active mirror at individual positions to compensate for aberrations in the patient's eye at the examination field.

41. In a combination as set forth in claim 40,
the first focussing means including an entrance pupil disposed at the particular distance from the examination field,
the second focussing means including a pinhole disposed at the paticular distance from the potodetector means.

42. In a combination as set forth in claim 42,
the light beam having a wavelength in the order of approximately 325–400 nanometers, and
the second scanning frequency being lower than the first scanning frequency.

43. A method of measuring the characteristics of a patient's eye at different positions in an examination field, including the steps of:
providing a beam of light,
directing the beam of light passing through an entrance pupil to the examination field, the examination field being displaced by a particular distance from the entrance pupil,
focussing the beam at the entrance pupil,
directing through a pinhole to a photodetector the light reflected by the patient's eye in the examination field, the photodetector being displaced by the particular distance from the pinhole,
focussing the reflected beam on the pinhole,
processing the signals produced by the photodetector to measure the characteristics of the patient's eye at the different positions in the examination field,
measuring aberrations in the characteristics of the patient's eye at different positions in the examination field, and
compensating in the light beam for the aberrations in the characteristics of the patient's eye at the different positions in the examination field.

44. A method as set forth in claim 43, including the steps of:
scanning in the examination field at a first frequency the light beam directed through the entrance pupil to obtain the production by the photodetector of signals representing the characteristics of the patient's eye at individual positions in the examination field,
scanning in the examination field, at a second frequency different from the first frequency, a portion of the light beam directed through the first pinhole,
detecting the light reflected from the patient's eye and scanned at the second frequency to produce signals representative of such detected light, and
processing the last mentioned signals to produce correctional signals representing the aberrations in the characteristics of the characteristics of the patient's eye in the examination field.

45. A method as set forth in claim 44, including the steps of:
disposing an active mirror adjustable at individual positions in the mirror,
including the active mirror in the path of the light beam scanned at the first frequency, and
adjusting the characteristics of the active mirror at individual positions in the active mirror in accordance with the characteristics of the correctional signals.

46. A method as set forth in claim 45 wherein
the light beam has a wavelength in the order of 325–440 nanometers.

47. A method of measuring the characteristics of a patient's eye at different positions in an examination field, including the steps of:
providing a beam of light,
directing the beam of light in a path through an entrance pupil to the examination field, the examination field being displaced by a particular distance from the entrance pupil,
focussing the beam at the entrance pupil,
directing through a pinhole to a photodetector the light reflected by the patient's eye in the examination field, the photodetector being displaced by the particular distance from the pinhole,
focussing the the reflected beam on the pinhole,
processing the signals produced by the photodetector to measure the characteristics of the patient's eye at the different positions at the examination field,
providing in the path of the light beam to the first pinhole a member with characteristics at different positions to adjust the examination field being scanned on the patient's eye, and
adjusting the characteristics of the adjustable member at the different positions to provide controlled variations of the examination field being scanned at the patient's eye.

48. A method as set forth in claim 47, including the steps of:

determining aberrations in the characteristics of the patient's eye at individual positions in the examination field being scanned, and adjusting the charactistics of the member at individual positions to compensate for variations in the characteristics of the patient's eye at the individual positions in the examination field being scanned.

49. A method as set forth in claim 48 wherein the signals are produced at the photodetector by a scan of the light beam in the examination field at a first frequency and wherein the aberrations of the light beam in the examination field are determined by a scan of the light beam in the examination field at a second frequency different from the first frequency.

50. A method as set forth in claim 49 wherein the examination field is at the front of the patient's eye and the light beam has a wavelength in the order of approximately 325-440 nanometers.

* * * * *